United States Patent
Algreatly

(10) Patent No.: US 9,367,651 B2
(45) Date of Patent: Jun. 14, 2016

(54) 3D WEARABLE GLOVE SCANNER

(71) Applicant: Cherif Atia Algreatly, Newark, CA (US)

(72) Inventor: Cherif Atia Algreatly, Newark, CA (US)

(73) Assignee: CHERIF ALGREATLY, Fremont, CA (US)

( * ) Notice: Subject to any disclaimer, the term of this patent is extended or adjusted under 35 U.S.C. 154(b) by 212 days.

(21) Appl. No.: 14/270,354

(22) Filed: May 5, 2014

(65) Prior Publication Data

US 2014/0375769 A1     Dec. 25, 2014

Related U.S. Application Data

(60) Provisional application No. 61/854,998, filed on May 6, 2013.

(51) Int. Cl.
| | |
|---|---|
| *H04N 13/02* | (2006.01) |
| *G06F 17/50* | (2006.01) |
| *G01B 7/004* | (2006.01) |
| *G01N 29/00* | (2006.01) |

(52) U.S. Cl.
CPC ............... *G06F 17/50* (2013.01); *G01B 7/004* (2013.01); *G01N 29/00* (2013.01)

(58) Field of Classification Search
None
See application file for complete search history.

(56) References Cited

U.S. PATENT DOCUMENTS

| | | | | |
|---|---|---|---|---|
| 2003/0068079 A1* | 4/2003 | Park | ............ | A61C 13/0004 382/154 |
| 2004/0195310 A1* | 10/2004 | Silverbrook | ............ | G06F 3/014 235/375 |
| 2007/0273687 A1* | 11/2007 | Daniel | ............ | G01B 11/2518 345/420 |
| 2009/0266898 A1* | 10/2009 | Miller | ............ | G06K 7/0004 235/472.01 |

* cited by examiner

*Primary Examiner* — Hung Dang

(57) ABSTRACT

Disclosed is a 3D scanner in the form of a wearable glove that can be worn by a user to swiftly scan the objects that the user touches. Touching the edges or corners of the object is enough for the present invention to automatically generate the necessary 3D model of the object. The user can scan an object with holes regardless of the object's size. The wearable glove is thin and light, and can be folded and carried in the user's pocket ready for use at any time or place.

19 Claims, 12 Drawing Sheets

| Tension Force Magnitude | Positions of Small Spots Relative to the Base Point | | | | | | | | | | | |
|---|---|---|---|---|---|---|---|---|---|---|---|---|
| | Small Spot #1 | | | Small Spot #2 | | | ....... | | | Small Spot #n | | |
| | X | Y | Z | X | Y | Z | X | Y | Z | X | Y | Z |
| 10U | | | | | | | | | | | | |
| 11U | | | | | | | | | | | | |
| 12U | | | | | | | | | | | | |
| 13U | | | | | | | | | | | | |
| 14U | | | | | | | | | | | | |
| 15U | | | | | | | | | | | | |
| 16U | | | | | | | | | | | | |
| 17U | | | | | | | | | | | | |
| 18U | | | | | | | | | | | | |
| 19U | | | | | | | | | | | | |
| 20U | | | | | | | | | | | | |
| 21U | | | | | | | | | | | | |
| 22U | | | | | | | | | | | | |

FIG. 9

3D WEARABLE GLOVE SCANNER

CROSS-REFERENCE TO RELATED APPLICATION

This application claims the benefits of a U.S. Provisional Patent Application No. 61/854,998, filed May 6, 2013.

BACKGROUND

Commercially available 3D scanners have various disadvantages and limitations. For example, some 3D scanners are heavy devices that cannot be carried without inconvenience, while others are heavy equipment that do not budge from their initial positions. Many 3D scanners share a perplexing trait with cameras: they cannot collect data about object surfaces that are hidden or not within the view field. Optical 3D scanners experience difficulties in scanning shiny, mirror like, or transparent objects. Moreover, the scanning mechanism of the commercially available 3D scanners is not easily executable. For most situations, a single scan will not produce a complete model of the subject. Multiple scans, even hundreds from many different directions, are usually required to obtain complete information about the sides of the object. Additionally, 3D scanners are not cheap, which limits their spread compared to other related devices or tools, such as 3D printers which can print the 3D model of a scanned object.

Nowadays, there is a real need for a type of 3D scanner that is easy to carry, and can scan holes and hidden parts of objects regardless of the surface properties of the scanned object. This new 3D scanner should be substantially cheaper and efficient to serve various medical, engineering, manufacturing, entertainment, and educational applications.

SUMMARY

The present invention disclose an innovative 3D scanner in the form of a wearable glove that can be worn by a user to simply scan objects that the user touches. The present invention has numerous advantages over other commercially available 3D scanners in the market. For example, the glove is very light and thin, and looks like a satin glove and can be worn while working simultaneously on a computer. It works indoors and outdoors with no light constraints, working equally well in both dark and well lighted environments. The glove can scan various objects of different sizes, starting with the size of a small finger ring to the size of a big car. The glove can easily recognize and scan holes or parts of the objects that are hidden from the user's line of sight. Moreover, the glove is water resistant and can scan objects located underwater once they are touched by the user's hands. Also, the glove does not experience difficulties when scanning objects with shiny, reflective, or transparent surfaces. The glove utilizes an existing hardware technology which easily and inexpensively carries out the present invention in comparison to other currently available 3D scanners in the market.

In one embodiment of the present invention, to scan a small object the user holds the object with one hand and touches the object with the other hand while wearing a glove in each hand. Each point or spot touched by a finger is immediately scanned. Touching all points of the object allows the construction of the 3D model of the object in real time on a device display, such as a mobile phone, tablet, or computer. In another embodiment of the present invention, to scan a big object the user touches the object with one or two hands while wearing the gloves. In one embodiment, touching the edges or corners of the surfaces of a big object is enough to scan the 3D model of the object without having to touch the entire points of the object's surfaces. This greatly simplifies and speeds up the scanning process.

The simplicity and ease-of-use of the present invention creates numerous innovative applications that serve different fields. For example, in the medical field, a parent can periodically use the glove to scan the body of his/her baby and monitor the changes of the baby's body over a period of time. Also, a patient can scan a part of his/her body at home over a period of time and provide his/her physician with this data, and the physician can use this data to clearly view the changes in the volume or shape of the patient's body. This simplifies the diagnosis or monitoring of the patient's medical condition. In the real estate field, a person can scan an existing home, including its walls, floors, doors, and windows, to create a 3D model of the home and present this 3D model on the Internet to be accessible to other people who might be interested in viewing the home but cannot physically visit it. In this case, people can walk through the virtual 3D model on a computer display to view the interior and exterior details of the home.

In 3D printing, the user can easily copy different objects by scanning them with the glove and printing the 3D models of these objects using a 3D printer available at home or online. This simplicity or ease-of-use is important especially with the current trend of at home 3D printers which are lacking a simple and cheap 3D scanner accessible to everyone. In the manufacturing and design field, engineers and designers can swiftly scan their prototypes with the gloves of the present invention in order to easily document or modify the 3D virtual model of the prototype on a computer display and print it again using a 3D printer.

Overall, the above Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 9 illustrates a table representing a database that associates the locations of the small spots, divided along the glove, with each magnitude of a tension force exerted on a string.

DETAILED DESCRIPTION

The present invention discloses a wearable glove that can be worn by a user to scan various objects within the reach of the user's hand. The user can hold the object in one hand and touch the object with the other hand. In this case, two gloves are worn on the left and right hands of the user. Each glove is equipped with a first sensing unit, a second sensing unit, and a third sensing unit. The first sensing unit detects the points of contact between the glove and the object. The second sensing unit detects the change of the glove's shape because of the user's finger movement. The third sensing unit detects the location of the glove relative to a reference point. Analyzing the data collected from each sensing unit allows a computer system to construct a 3D model of the object and present it on a computer display.

Figure 1:
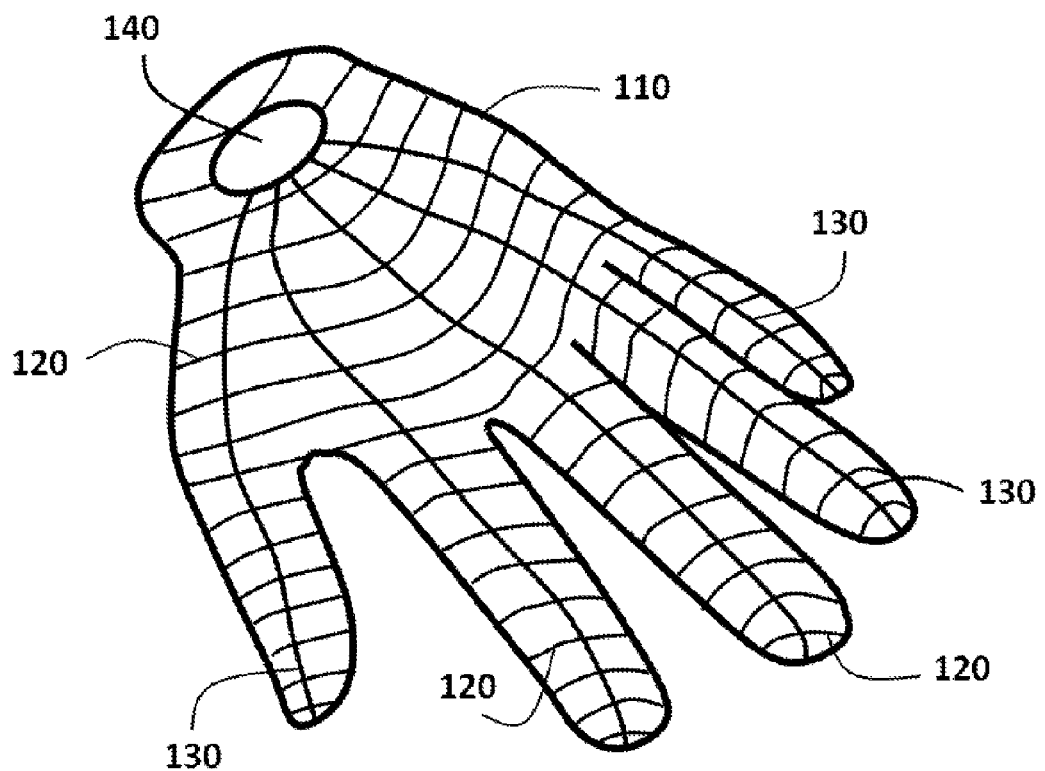
FIG. 1 illustrates a wearable glove that functions as a 3D scanner, according to one embodiment of the present invention.

FIG. 1 illustrates the glove 110 of the present invention, according to one embodiment. The first sensing unit 120 is in the form of multiple touch sensors embedded within the textile of the glove to cover the entire glove surface. Once the user touches an object with the glove, the touch sensors sense the points of contact between the glove and the object. The second sensing unit 130 is in the form of five flexible strings that connect the five ends of the gloves at each fingertip to a fixed point located near the opening of the glove. The five strings are also embedded within the textile of the glove. Each string of the five strings expands or contracts according to the movement of a finger which exerts a tension force on the string. The magnitude of this tension force is sensed by a sensor. A database that associates each unique tension force with a finger movement is utilized. Sensing the magnitude of the tension force and checking it against the database allows the detection of the finger's movement in real time. The third sensing unit 140 detects the location of a base point located on the glove relative to a reference point that has a fixed position near the user.

The surface of the glove is divided into small spots, each of which has a defined location on the glove's surface relative to the base point. A touch sensor of the first sensing unit is attached to each small spot of the glove's surface. In one embodiment, the touch sensor is in the form of an ON/OFF button that turns "ON" when it is touched or pressed, and turns "OFF" when it is released. When the user moves his/her finger to touch an object the shape or configuration of the glove changes because of finger movement or bending. At this moment, the second sensing unit detects the change of the shape or configuration of the glove and determines the new location of each small spot relative to the base point. Moving the user's hand changes the position of the glove, and the third sensing unit tracks the current position of the base point relative to the reference point. Determining the location of the base point relative to the reference point, and the position of the small spots that touched the object, relative to the base point, allows detecting the location of the object's points that are in contact with the glove. Touching the points of the object by the glove generates a points cloud that can be reconstructed to create a virtual 3D model of the object that is presented on a computer display.

Figure 2:
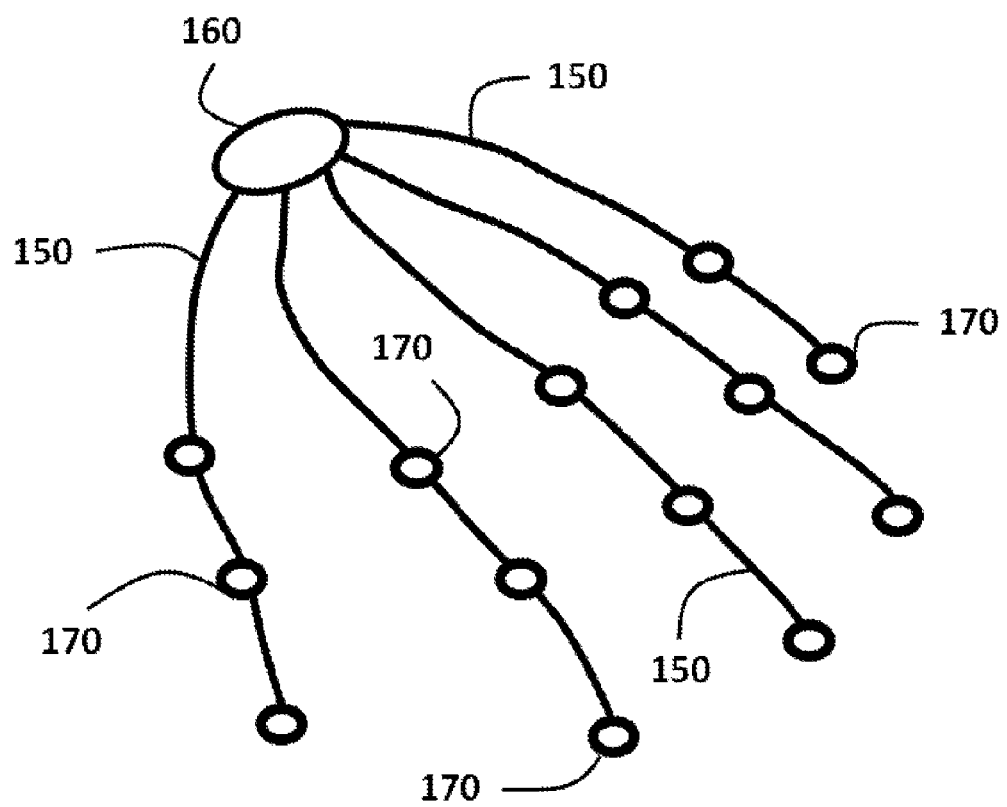
FIGS. 2 and 3 illustrate sensing the movement of the hand's fingers and the touch of the scanned object by the first and second sensing units of the present invention.
Figure 3:
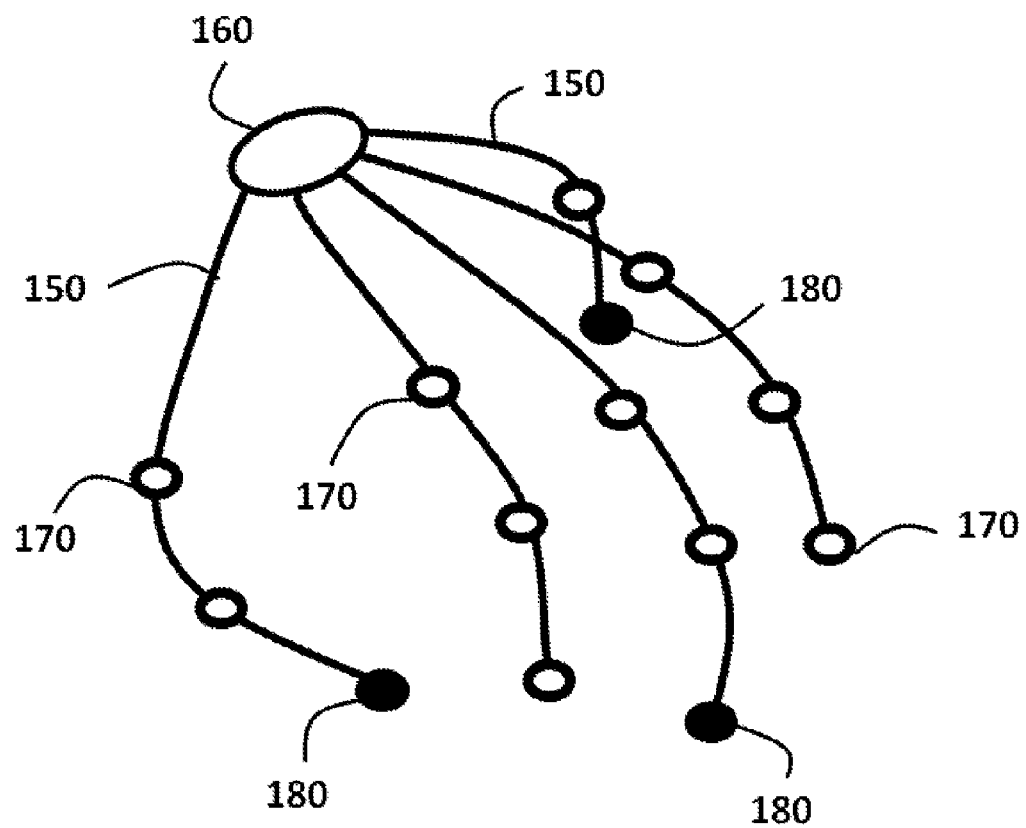

FIG. 2 illustrates the five strips 150 of the second sensing unit and the third sensing unit 160. The figure also illustrates a plurality of touch sensors 170 located on top of the five strings. As mentioned previously, the touch sensors are spread all over the glove surface and are not only on the top of the flexible strips. In this example, for a demonstrative purpose, some touch sensors are located on top of the five strings. FIG. 3 illustrates changing the shapes of the five strings 150 because of the movement of the user's fingers to touch an object. Some of the touch sensors 170 remain "OFF" or untouched, while other touch sensors 180 are turned "ON" when they make contact with the object. Generally, turning a touch sensor "ON" is an indication for pressing the touch sensor with the object when they are in contact with each other.

In this example, each time a finger moves the magnitude of the tension force exerted on the string of the finger is sensed by the second sensing unit. Comparing this magnitude with the database determines the current movement of the finger. According to the current movement of the finger, the positions of the small spots located on the finger are determined relative to the base point. Touching the object during this movement turns some touch sensors "ON". These touch sensors are associated with certain small spots with known current positions. Accordingly, the locations of the object's points that are in contact with the touch sensors are then determined. Storing the locations of these points, while using the movement of the hand's fingers to touch more points on the object's surfaces, creates a points cloud that represents the object's surface. The reconstruction of the points cloud creates the virtual 3D model of the object.

In one embodiment of the present invention, the user wears one glove on one hand, or two gloves on two hands, to scan an object located in a fixed position. The object does not move during the scanning. In another embodiment, the user wears two gloves, one on the left hand and another one on the right hand, to carry the object in one hand and scan it with the other hand. In such a case, the user can move while carrying the object and this movement does not impact the scanning process. Carrying the object during the scanning process allows the user to navigate to a desk in front of a computer display to view the gradual creation of the 3D model while scanning the object.

In one embodiment of the present invention, touching the edges of the object is enough to scan the skeleton of the object. In this case, the surfaces of this skeleton are automatically constructed during the creation of the 3D model of the object. In this case, the user adjusts the setting of the glove to interpret the collected points cloud as edges of the scanned object. If the user mistakenly touches a point of the object that is not located on an edge, this point is automatically ignored during the construction of the 3D model. This is achieved through the software program, which creates the 3D model. It functions so that any scanned point located inside a scanned polygon of the same plane is ignored. Generally, scanning an object by touching its edges simplifies the scanning process for the user.

In another embodiment of the present invention, touching the corners of each surface of the object is enough to create the 3D model of the object. This is done by automatically connecting the corners of each surface and filling out this surface to create the 3D model on a computer display. In this case, the user adjusts the setting of the glove to interpret the collected points cloud as corners of surfaces. If the user mistakenly touches a point on the object that is not located on a corner, this point is automatically ignored during the construction of the 3D model. To achieve this, the software program checks if there is a point located inside a polygon connecting a group of corners of the same plane, and once such a point is found it is ignored or deleted. Also, scanning an object by touching its corners dramatically simplifies and speeds up the scanning process for the user.

In one embodiment, the glove is equipped with a digital camera that captures the picture of the object's surfaces. This picture is used to overlay the surfaces of the 3D model on the computer display to replicate the color, material, or appearance of the scanned object. In another embodiment, the camera captures the picture of the background behind the object from different points of view when the glove is moved near the object. In this case, these pictures are used to present the 3D model of the object on a computer display with a real background from different points of view. In other words, when horizontally or vertically rotating the 3D model on the computer display, with each rotation, the picture of the real background appears behind the 3D model. This feature can be an option for the user, according to his/her needs or preference, but in general, presenting the 3D model with its background is valuable in many cases and applications In one embodiment, the glove is equipped with a sensor that senses the temperature, pressure, or elasticity of the scanned object. This is highly useful in many medical applications when scanning a human body by the present invention. In this case, the 3D model of the scanned body will be tagged with temperature, pressure, elasticity, or other collected data of each part of the body, as well as, the date of scanning. Such information is useful for medical analysis, especially when changes in the shape of the body occur over a period of time with an association of changes in temperature, pressure, elasticity, or the like.

Figure 4:
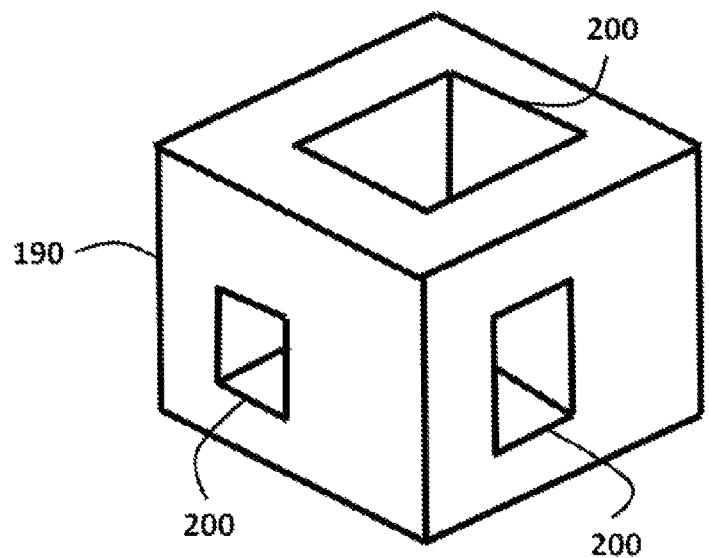
FIGS. 4 and 5 illustrate two examples of objects that include holes where the present invention can recognize and scan these holes.
Figure 5:
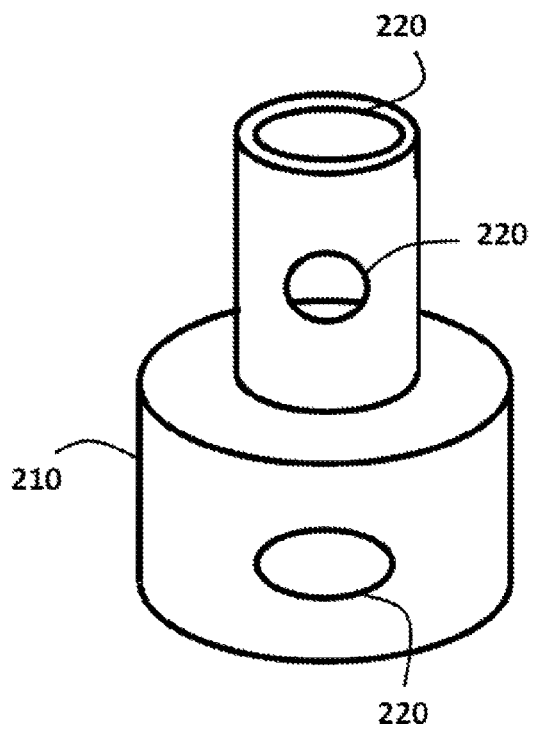

One of the main advantages of the present invention is allowing the user to scan objects that include holes or voids. For example, FIG. 4 illustrates an object 190 with three holes 200, and FIG. 5 illustrates another object 210 with two holes 220. To scan such objects, the user touches the exterior surfaces of the object and also inserts his/her finger inside the holes to touch the interior surfaces of each hole. If a hole is too deep for the user's hand or fingers to reach, touching the edges or the corners of the hole is enough to scan the entire surfaces around the hole, as was described previously. Using the capability of the present invention to scan holes or voids differentiates the present invention from other traditional 3D scanners which cannot perform such scanning of holes.

Figure 6:
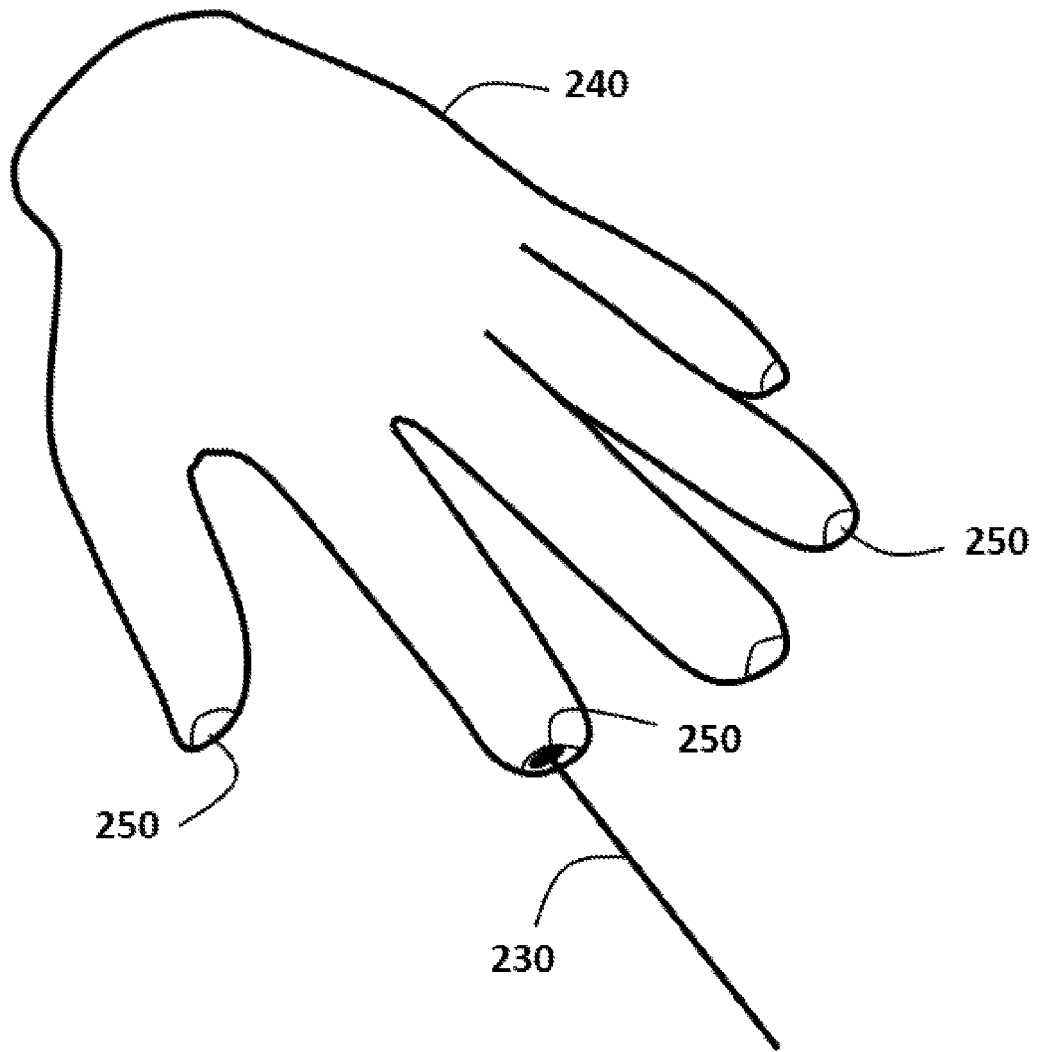
FIG. 6 illustrates an extension cord used with the glove of the present invention to allow the user to scan objects that are out of reach of his/her hand.

In one embodiment of the present invention, to touch an object that is not within the reach of the user's hand, an extension cord extends from the glove from a fingertip to touch the object in place of the user's finger. For example, FIG. 6 illustrates an extension cord 230 extending from a glove 240 at the position of a fingertip 250. This extension cord comes out of any finger, according to the user's needs or preference. The extension cord is always aligned to be parallel to the slope of its fingertip where this slope can be detected by the data collected via the second sensing unit. The length of the extension cord can be increased until it reaches the object. Once the extension cord touches the object, the value of its length is registered to generate the points cloud of the object. The extension cord is a perfect solution to reach deep holes that are difficult to be reached with just the user's finger, regardless of whether these holes are too far or too thin to insert a finger. It is also a practical solution to reach the corners or edges of high objects such as walls, rooms, or buildings when using the corners or edges scanning technique, as was described previously.

In another embodiment of the present invention, the glove is equipped with a 3D compass that detects the tilting or rotation of the user's hand relative to the xy-plane. This information is important when determining the location of the object's points touched by the glove when the user's hand is tilted or rotated. In the case of using two gloves, each one of the two gloves will be equipped with a 3D compass.

As mentioned previously, the present invention utilizes an existing hardware technology which easily and inexpensively carries out the functions of the present invention compared to other currently available 3D scanners in the market. For example, in one embodiment, the touch sensors of the first sensing unit can be "ON/OFF" buttons similar to the keys found on a computer keyboard. Each button has an ID and turns "ON" when it is pressed when touching an object, and turns "OFF" when it is released. Each "ON/OFF" button is attached to a small spot of the small spots that divide the entire glove surface. This dividing includes the top and bottom sides of the glove surface. The position of each small spot, relative to the base point, is always tracked by the second sensing unit. Accordingly, the position of the "ON" touch sensors is determined relative to the base point in real time. The positions of the "ON" touch sensors represent the locations of the object's points that are in contact with the glove. In another embodiment, the first sensing unit is in the form of a touch surface that utilizes the same technology used in touchscreens, such as resistive technology or capacitive technology, as known in the art.

Figure 7:
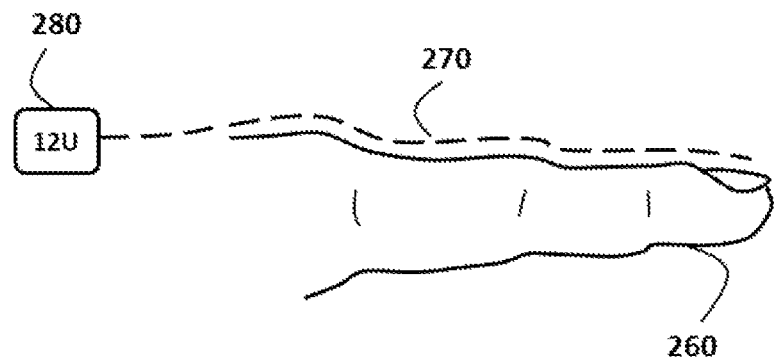
FIGS. 7 and 8 illustrate the detection of the movement of a hand's finger using a single string, according to one embodiment of the present invention.
Figure 8:
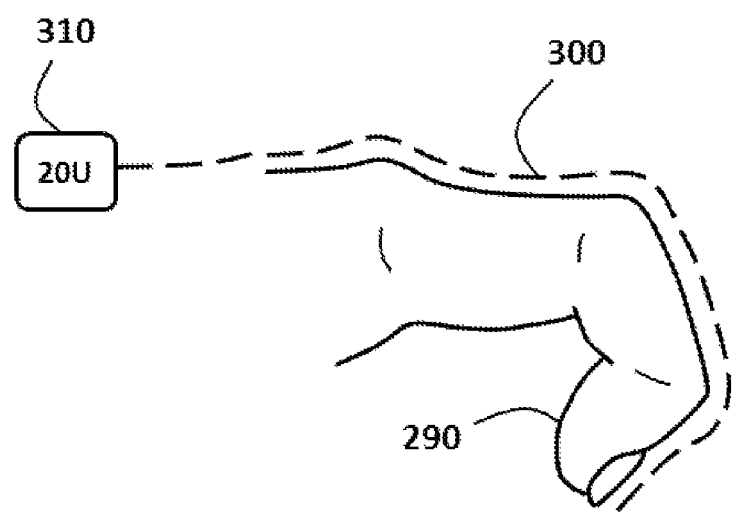

The second sensing unit is comprised of five flexible strings connected to five sensors that measure the tension force in each string. For example, FIG. 7 illustrates a user's finger 260 in an extended, straight position with a string 270 of the five strings located on top of the finger. The string is connected to a sensor 280 that senses the magnitude of tension exerted by the stretching of the string because of the finger's movement or bending. As shown in the figure, the finger's position exerts a tension force on the string equal to "12 units", as indicated by the rectangle that represents the sensor. FIG. 8 illustrates bending the same finger 290, where the string 300 is stretched to increase the tension force exerted on the sensor 310. As shown in the figure, at this finger position, the tension force exerted on the string is equal to "20 units", as indicated by the rectangle that represent the sensor in the figure.

Figure 10:
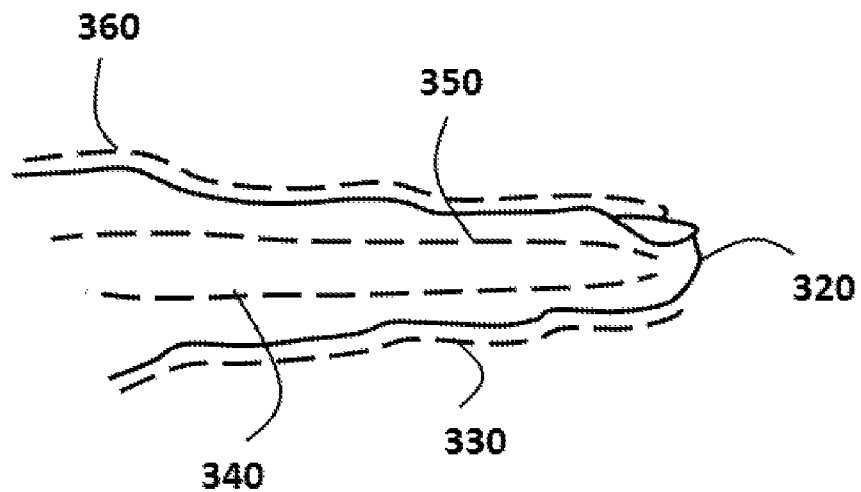
FIGS. 10 and 11 illustrate the detection of the movement of a hand's finger using four strings, according to one embodiment of the present invention
Figure 11:
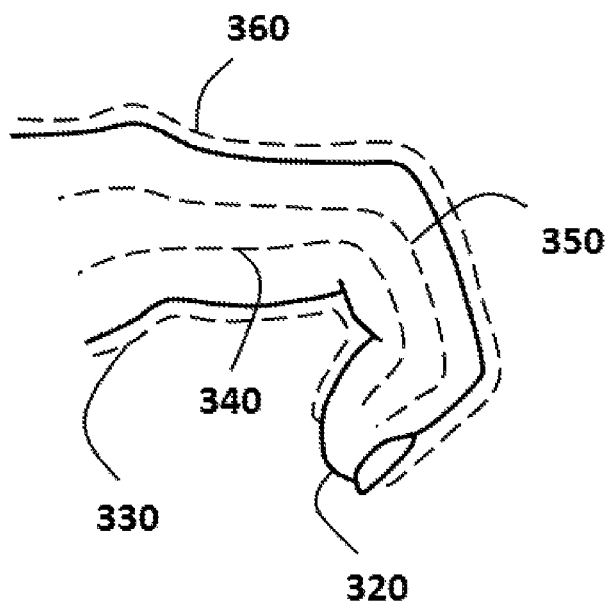

FIG. 9 illustrates an example of a table representing a database that associates each magnitude of a tension force exerted on the string with a location of each small spot relative to the base point, as was described previously. As shown in the table, the tension force can be less than "12 units" when the user bends his/her finger upward. Also, the tension force can be greater than "20 units" when the user bends his/her finger downward, greater than what is shown in FIG. 8. The number of small spots may differ from glove to glove according to the needed accuracy of the scanning. The greater number of small spots that divide the glove, the more sensitive scanning the user can obtain In one embodiment, the fives string of each glove can be greater than five. For example, two or more strings may be assigned to each finger of the glove. The advantage of using two or more strings is that there is more accuracy in sensing the finger's movement, especially when the finger is moved horizontally. For example, FIG. 10 illustrates a user's finger 320 with four strings 330-360 attached to the finger, via the glove, from four sides. FIG. 11 illustrates the same finger when it is bent, where the magnitude of the tension force exerted on each one of the four string changes. Accordingly, the detection of the finger's movement will be more accurate than using a single string. In another embodiment, the second sensing unit replaces the strings with mechanical trackers that are positioned at each joint of the user's hand or fingers to rotate with the joints' rotations and track these rotations. Tracking the joints' rotations allows the detection of the movement of the user's fingers, as known in the art.

The third sensing unit tracks the location of the base point, located on the glove, relative to a fixed reference point located near the user, using one of the known positioning system. In one embodiment, the time and flight system is used to determine the distance by measuring the time of propagation of pulsed signal between a transmitter located at the base point and three receivers located at three reference points near the user. In this case, Ultrasonic trackers can be used since they do not need a line of sight between the transmitter and the three receives. Also, Radio waves can be used instead of the Ultrasonic waves. In another embodiment, inertial sensing technology is used to detect the position of the base point relative to a default or start position. The main advantage of inertial sensing is that it does not require the external reference of the reference point. Instead, it measures rotation with a gyroscope and position with an accelerometer with respect to a known starting position and orientation.

In one embodiment of the present invention, the third sensing unit utilizes a mechanical linkage. This type of tracking system uses mechanical linkages between the reference point and the glove. Two types of linkages can be used. One is an assembly of mechanical parts that can each rotate, providing the user with multiple rotation capabilities. The orientation of the linkages is computed from the various linkage angles measured with incremental encoders or potentiometers. Other types of mechanical linkages that can be used are wires that are rolled in coils. A spring system ensures that the wires are tensed in order to measure the distance accurately. The degrees of freedom sensed by mechanical linkage trackers are dependent upon the constitution of the tracker's mechanical structure, as known in the art.

Figure 12:
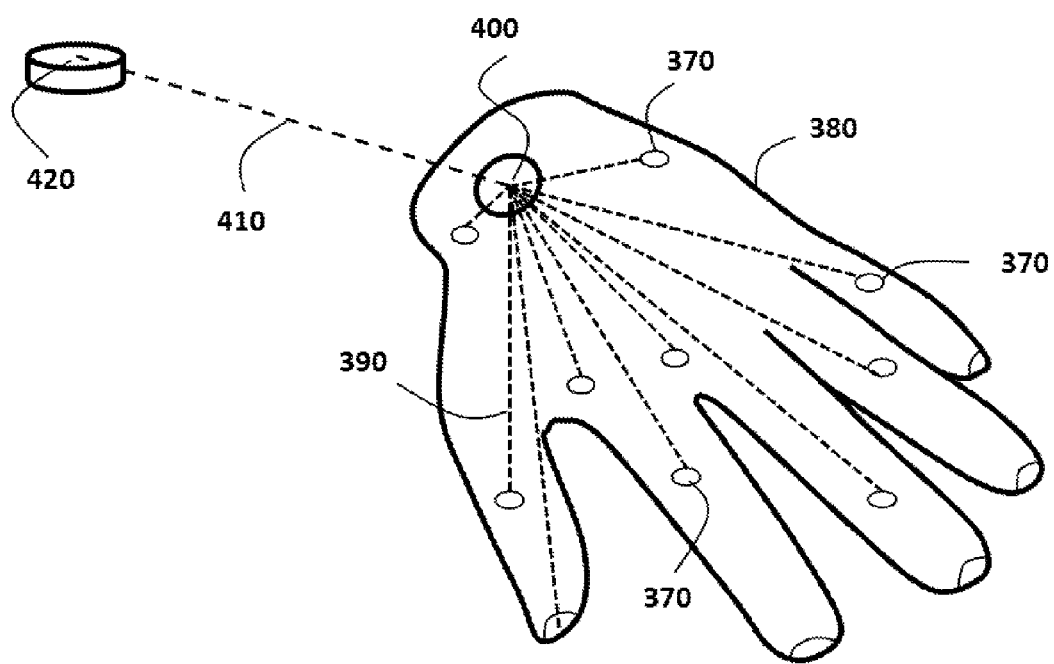
FIG. 12 illustrates the detection of the positions of the small spots relative to a base point located on the glove and a reference point located near the user.

FIG. 12 illustrates how the locations of the small spots are related to the position of the base point, which is subsequently related to the reference point location. As shown in the figure, a plurality of small spots 370 are located on a glove 380, where the dotted lines 390 represent the location of each small spot relative to the base point 400. The dotted line 410 represents the location of the base point relative to the reference point 420. Accordingly, the location of each small spot relative to the reference point can be determined in real time while moving the glove with the user's hand.

Figure 13:
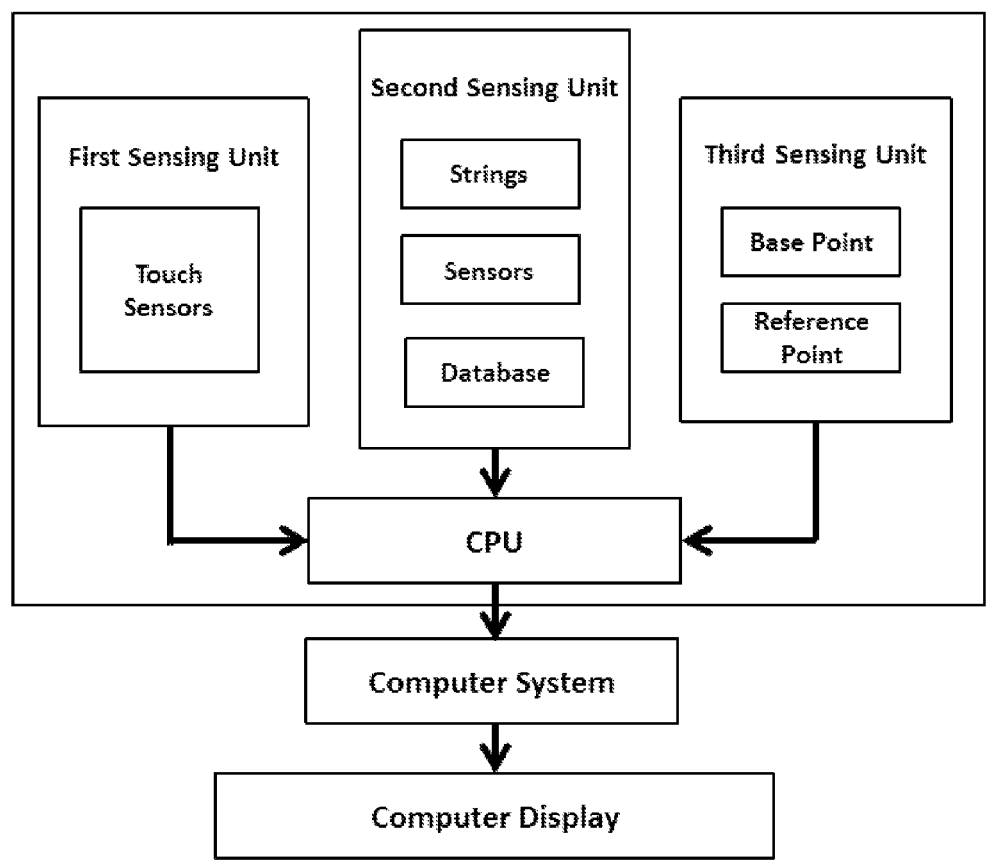
FIG. 13 illustrates a block diagram presenting the main components of the present invention, according to one embodiment.

FIG. 13 illustrates a block diagram indicating the main components of the present invention, according to one embodiment. As shown in the block diagram, the present invention is comprised of three sensing unit. The first sensing unit is comprised of a plurality of touch sensors. The second sensing unit is comprised of strings, sensors, and a database. The third sensing unit is comprised of a base point located on the glove and a reference point located near the glove. The three sensing units are connected to a CPU that receives the outputs of each sensing unit and generates the points cloud that represents the surface of the scanned object. The data of the points cloud is provided to a computer system that constructs the 3D model of the scanned object and presents it on a computer display.

Figure 14:
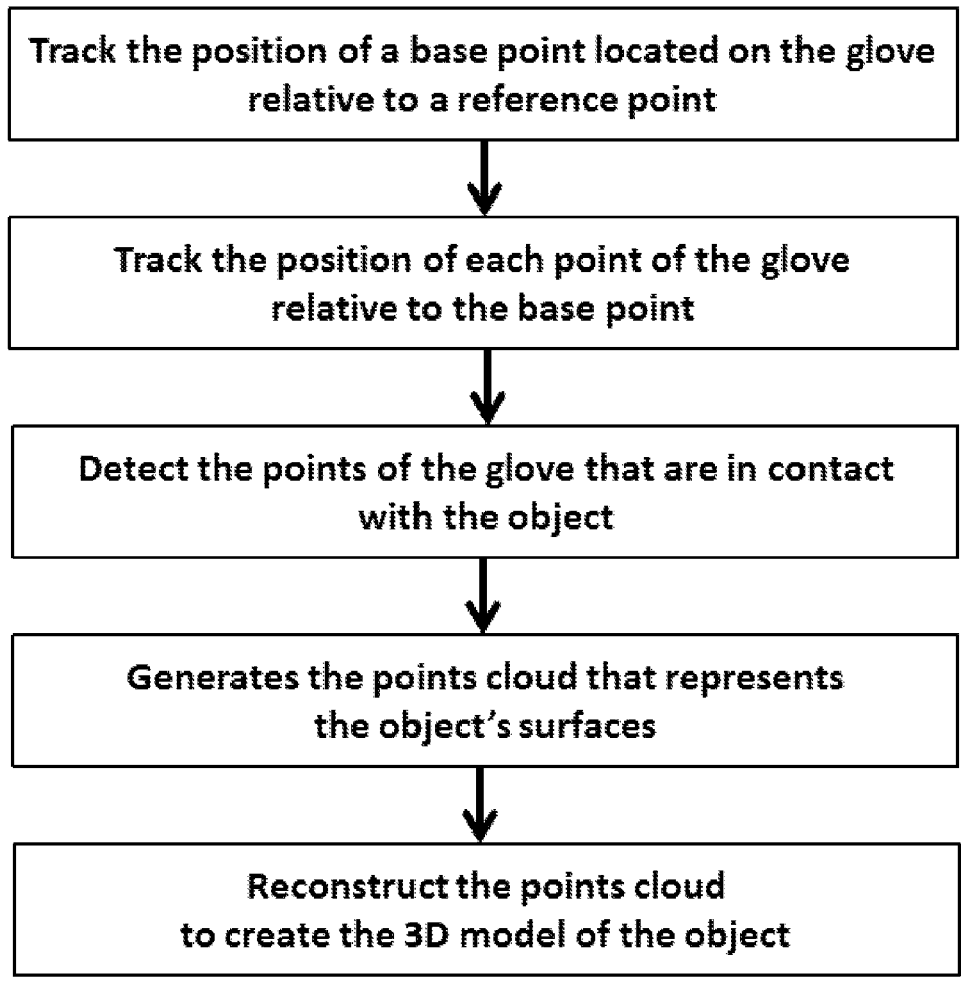
FIG. 14 illustrates a block diagram indicating the scanning steps of the method of the present invention, according to one embodiment.

FIG. 14 illustrates a block diagram representing the scanning method of the present invention, according to one embodiment. As shown in the block diagram, the method of the present invention is comprised of five technical steps. The first step is to track the position of a base point, located on the glove, relative to a reference point. The second step is to track the position of each point of the glove relative to the base point. The third step is to detect the points of the glove that are in contact with the object. The fourth step is to generate the points cloud that represents the object's surface. The fifth step is to reconstruct the points cloud to create the 3D model of the object.

As discussed previously, the present invention of 3D wearable glove scanner is easy to carry, and can scan holes and hidden parts of objects regardless of the surface properties of the scanned object (such as shiny, reflective, or transparent surface material). It is water resistant and can scan objects located underwater once they are touched by the user's hands. It is also substantially cheaper than traditional 3D scanners which makes it a perfect scanning tool to server various medical, engineering, manufacturing, entertainment, and educational applications.

Figure 15:
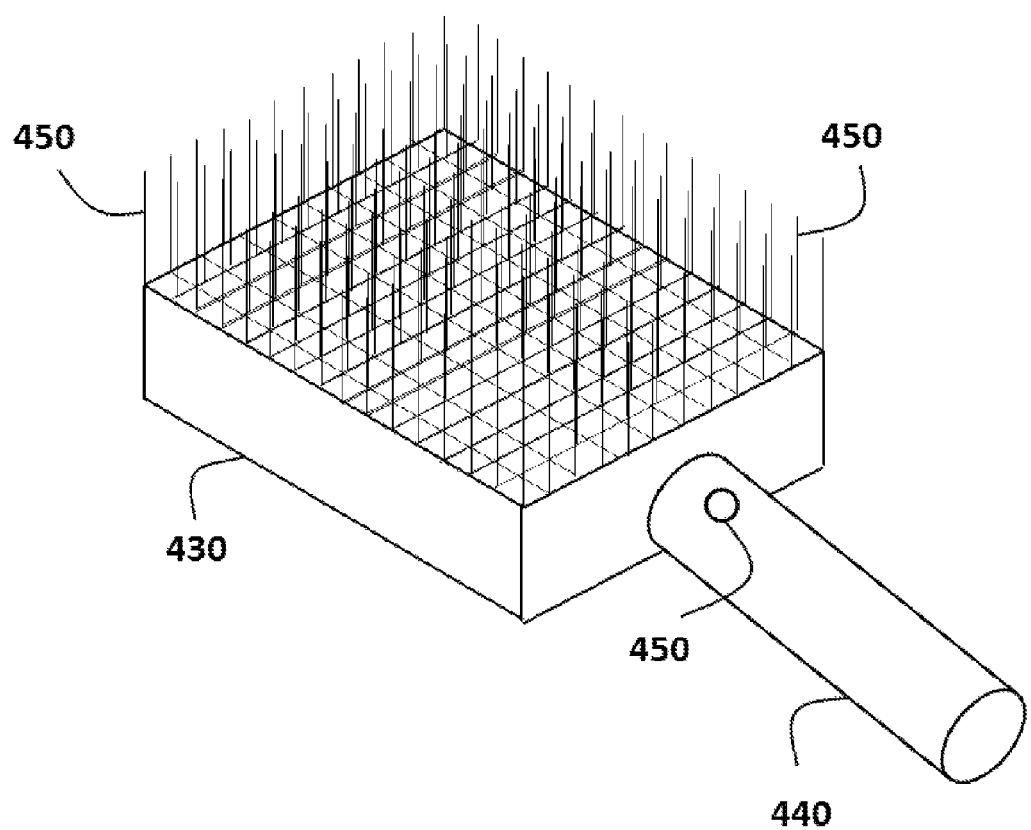
FIG. 15 illustrates a 3D scanner in the form of a brush that can be held by a user's hand to scan objects once it touches them, according to one embodiment of the present invention.

Finally, it is important to note that the present invention can take forms other than a wearable glove. For example, in FIG. 15, the present invention is in the form of a brush 430 that has a handle 440 where the user can hold the handle to carry the brush. The brush includes a plurality of thin sticks 450 that move up and down when they are pushed to touch an object. Each thin stick has a defined location on the brush, and the change in length of each thin stick is detected by a first sensing unit. The brush can be tilted or rotated by the user's hand where this tilting or rotation is detected by a second sensing unit which utilizes a 3D compass. The brush has a base point 450 located on its surface where a third sensing unit tracks the position of the base point relative to a reference point located near the brush.

Conclusively, while a number of exemplary embodiments have been presented in the description of the present invention, it should be understood that a vast number of variations exist, and these exemplary embodiments are merely representative examples, and are not intended to limit the scope, applicability or configuration of the disclosure in any way. Various of the above-disclosed and other features and functions, or alternative thereof, may be desirably combined into many other different systems or applications. Various presently unforeseen or unanticipated alternatives, modifications variations, or improvements therein or thereon may be subsequently made by those skilled in the art which are also intended to be encompassed by the claims, below. Therefore, the foregoing description provides those of ordinary skill in the art with a convenient guide for implementation of the disclosure, and contemplates that various changes in the functions and arrangements of the described embodiments may be made without departing from the spirit and scope of the disclosure defined by the claims thereto.

The invention claimed is:

1. A 3D scanner in the form of a wearable glove to scan an object wherein the 3D scanner is comprised of:
   a glove that can be worn on a user's hand to touch the object;
   a first sensing unit to detect the points on the glove that are in contact with the object;
   a second sensing unit to determine the current position of the points relative to a base point located on the glove;
   a third sensing unit to track the location of the base point relative to a reference point that has a fixed position; and
   a computer system that receives the output of the first sensing unit, the second sensing unit, and the third sensing unit to construct the 3D model of the object.

2. The method of claim 1 wherein the first sensing unit is a plurality of ON/OFF buttons.

3. The method of claim 1 wherein the first sensing unit is a touch surface utilizes resistive technology or capacitive technology.

4. The method of claim 1 wherein the second sensing unit is comprised of mechanical trackers that track the rotation of the joints of the user's hand.

5. The method of claim 1 wherein the third sensing unit measures the time of propagation of pulsed signal between a transmitter located at the base point and three receivers located at three reference points using Ultrasonic or Radio waves.

6. The method of claim 1 wherein the third sensing unit uses inertial sensing technology to detect the position of the base point relative to a default or start position.

7. The method of claim 1 wherein the third sensing unit utilizes a mechanical linkage between the reference point and the glove.

8. The method of claim 1 wherein the glove touches the edges of the object and the computer system automatically generates the 3D model of the object using the edges.

9. The method of claim 1 wherein the glove touches the corners of each surface of the object and the computer system automatically generates the 3D model of the object using the corners.

10. The method of claim 1 wherein the object includes holes that can be touched by the glove to be scanned.

11. The method of claim 1 further a digital camera is utilized to capture the picture of the object's surface and replicate the appearance of the object's surface on the 3D model.

12. The method of claim 1 further a digital camera is utilized to capture the picture of the background of the object to be presented behind the 3D model.

13. The method of claim 1 further an extension cord extends from the glove to touch the object wherein the length and slope of the extension cord are detected.

14. The method of claim 1 wherein two wearable gloves to be worn on two hands wherein one hand of the two hands carries the object and the other hand of the two hands touches the object.

15. The method of claim 1 further a 3D compass is utilized to detect the tilting or rotation of the glove.

16. The method of claim 1 further a sensor is utilized to sense the temperature, pressure, or elasticity of the object.

17. The method of claim 1 wherein the second sensing unit is comprised of strings connected to sensors that measure the magnitude of the tension forces exerted on the stings because of the movement of the user's hand.

18. The method of claim 17 wherein a database is utilized to associate each unique magnitude with locations of glove points.

19. A system for 3D scanning comprised of:
a container with movable sticks that can be carried by a user's hand to be in contact with an object wherein the lengths of the movable parts change when contacting the object;
a first sensing unit to detect the movable parts that are in contact with the object;
a second sensing unit to detect the change of lengths;
a third sensing unit to detect the location of the container relative to a reference point that has a fixed position; and
a computer system that receives the output of the first sensing unit, the second sensing unit, and the third sensing unit to construct the 3D model of the object.

* * * * *